US00PP29761P2

(12) United States Plant Patent
Legro et al.

(10) Patent No.: US PP29,761 P2
(45) Date of Patent: Oct. 16, 2018

(54) ***DELPHINIUM* PLANT NAMED 'RED LARK'**

(50) Latin Name: ***Delphinium* hybrid**
Varietal Denomination: Red Lark

(71) Applicant: Ball Horticultural Company, West Chicago, IL (US)

(72) Inventors: Robert A. H. Legro; Christa Kievit, Hem (NL); Robert B. Eisenreich, North Aurora, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/732,428

(22) Filed: Nov. 10, 2017

(51) Int. Cl.
*A01H 5/02* (2018.01)

(52) U.S. Cl.
USPC ..... Plt./423

(58) Field of Classification Search
USPC ..... Plt./423
See application file for complete search history.

*Primary Examiner* — Annette H Para
(74) *Attorney, Agent, or Firm* — Audrey Charles

(57) ABSTRACT

A new and distinct cultivar of *Delphinium* plant named 'Red Lark', characterized by its semi-double, light red-colored flowers, medium green-colored foliage, and moderately vigorous, upright growth habit, is disclosed.

2 Drawing Sheets

Latin name of genus and species of plant claimed: *Delphinium* hybrid.

Variety denomination: 'Red Lark'.

BACKGROUND OF THE INVENTION

The present invention relates to a new and distinct cultivar of *Delphinium* plant botanically known as *Delphinium* hybrid and hereinafter referred to by the cultivar name 'Red Lark'.

The new cultivar originated in a controlled breeding program in Enkhuizen, The Netherlands during August 2007. The objective of the breeding program was the development of *Delphinium* having a novel flower color and a compact growth habit.

The new *Delphinium* cultivar is the result of cross-pollination. The female (seed) parent of the new cultivar is the proprietary *Delphinium* hybrid breeding selection coded E112-1, not patented, characterized by its semi-double type, light red-colored flowers, medium green-colored foliage, and upright growth habit. The male (pollen) parent of the new cultivar is the proprietary *Delphinium* hybrid breeding selection coded E078-1, not patented, characterized by its semi-double type, salmon-red colored flowers, medium green-colored foliage, and upright-compact growth habit. The new cultivar was discovered and selected as a single flowering plant within the progeny of the above stated cross-pollination during August 2008 in a controlled environment in Venhuizen, The Netherlands.

Asexual reproduction of the new cultivar by in vitro propagation since October 2009 in West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Red Lark' as a new and distinct cultivar of *Delphinium* plant:

1. Semi-double, light red-colored flowers;
2. Medium green-colored foliage; and
3. Moderately vigorous, upright-compact growth habit.

Plants of the new cultivar differ from plants of the female parent primarily in having stronger stems and a more compact growth habit. Plants of the new cultivar differ from plants of the male parent primarily in having a different flower color.

Of the many commercially available *Delphinium* cultivars, the most similar in comparison to the new cultivar is 'Princess Caroline', not patented. However, in side by side comparisons, plants of the new cultivar differ from plants of 'Princess Caroline' in at least the following characteristics:

1. Plants of the new cultivar are shorter than plants of 'Princess Caroline'; and
2. Plants of the new cultivar have stronger stems than plants of 'Princess Caroline'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Red Lark'. The plants were grown in one-gallon containers for 12 weeks in a greenhouse in Elburn, Ill.

DETAILED BOTANICAL DESCRIPTION

Figure 1:
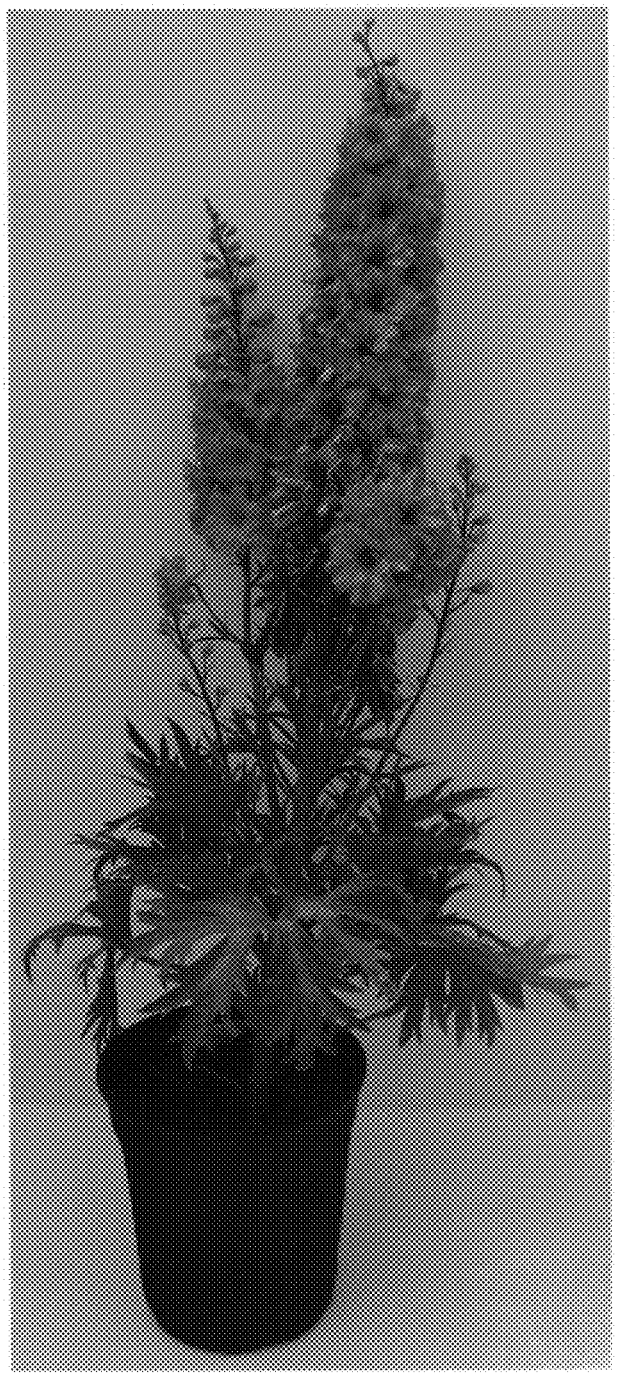
FIG. 1 illustrates a side view of the overall growth and flowering habit of 'Red Lark'.
Figure 2:
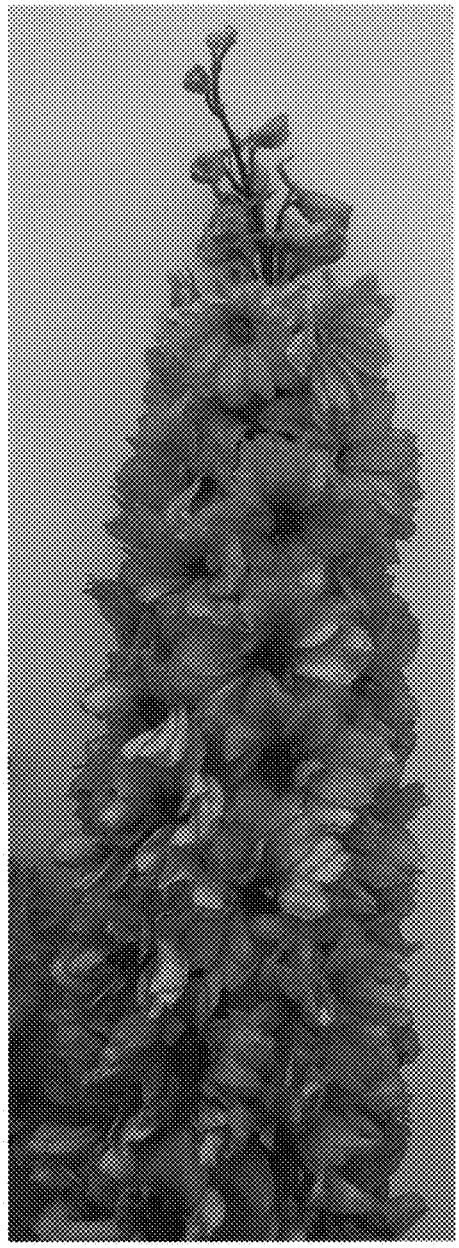
FIG. 2 illustrates a close-up view of an individual inflorescence of 'Red Lark'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in July 2013 under natural light conditions in West Chicago, Ill.

The following descriptions and measurements describe plants produced from in vitro plantlets and grown in a glass-covered greenhouse in one-gallon containers under conditions comparable to those used in commercial practice. The plants were grown in Elburn, Ill. in one-gallon containers for 12 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Delphinium* hybrid 'Red Lark'.

Parentage:

*Female parent*.—Proprietary *Delphinium* hybrid breeding selection coded E112-1, not patented.

*Male parent*.—Proprietary *Delphinium* hybrid breeding selection coded E 078-1, not patented.

Propagation:

*Type*.—In vitro propagation is preferred.

*Time to initiate roots*.—Approximately 4 to 5 weeks.

*Root description*.—Fibrous, brown in color.

*Rooting habit*.—Freely branching.

Plant description:

*Commercial crop time*.—Approximately 12 to 14 weeks from a tissue culture plantlet to finish in a one-gallon container.

*Growth habit and general appearance*.—Moderately vigorous, upright.

*Size*.—Height from soil level to top of plant plane: Approximately 70.5 cm. Width: Approximately 37.0 cm.

*Primary flowering stems*.—Quantity: Approximately 2. Strength: Strong. Length: Approximately 58.0 to 70.5 cm. Diameter: Approximately 7.0 mm to 1.3 cm. Length of central internode: Approximately 2.8 cm. Texture: Moderately pubescent, somewhat waxy. Color: 146A with an overlay of 187B.

Foliage description:

*General description*.—Quantity of leaves per main flowering stem: Approximately 12. Fragrance: None. Form: Simple. Arrangement: Rosette at plant base and alternate on flowering stems.

*Leaves*.—Aspect: Petiole is at an acute angle to stem and leaves are primarily perpendicular to stem. Shape: Palmately lobed. Margin: Incised, ciliate. Apex: Acute to acuminate. Base: Cordate. Venation pattern: Palmate. Length of mature leaf: Approximately 13.0 cm. Width of mature leaf at center of stem: Approximately 17.0 cm. Texture of upper surface: Glabrous. Texture of lower surface: Glabrous surface with pubescent venation. Color of upper surface of young and mature foliage: 137A with venation of 137B. Color of lower surface of young and mature foliage: Closest to 138B with venation of 138A.

*Petiole*.—Length: Approximately 7.5 cm. Diameter: Approximately 5.0 mm. Texture: Moderately pubescent. Color: 146B to 146A.

Flowering description:

*Flowering habit*.—'Red Lark' is freely flowering under outdoor growing conditions with substantially continuous blooming from late spring through summer.

*Lastingness of individual flower on the plant*.—Approximately 10 to 14 days.

Inflorescence description:

*General description*.—Type: Terminal raceme, persistent. Aspect: Erect, flowers face outward. Quantity per plant: Approximately 2. Fragrance: None detected. Length or height: Approximately 31 to 46 cm. Width: Approximately 10.5 cm. Quantity of fully open flowers per inflorescence: Approximately 45 to 60.

Flower description:

*Type*.—Semi-double, zygomorphic.

*Bud just before opening*.—Quantity per inflorescence: Approximately 8. Shape: Ovoid. Length: Approximately 2.6 cm, including spur. Diameter: Approximately 1.2 cm. Color: 144C and 37B in lengthwise stripes.

*Corolla*.—Shape: Round. Diameter: Approximately 5.0 cm. Depth: Approximately 2.2 cm.

*Petals/petaloids*.—Quantity: Approximately 22 petals and 2 to 3 irregularly-shaped petaloids arranged in several whorls. Shape: Obovate to oblong. Appearance: Dull. Margin: Entire. Apex: Acute. Base: Truncate. Length of outermost: Approximately 2.8 cm. Width of outermost: Approximately 1.7 cm. Length of innermost: Approximately 2.5 cm. Width of innermost: Approximately 1.2 cm. Texture of upper surface: Glabrous. Texture of lower surface: Glabrous with outermost petals sparsely pubescent on central stripe. Color of upper surface when first open: 48D with margins of 48A. Color of lower surface when first open: 48D with outermost petals having a central stipe of 144A with 144D. Color of upper surface when fully open: Closest to 52B to 52C. Color of lower surface when fully open: Closest to 48C with outermost petals having a central stipe of 144A with 144D.

*Sepals*.—None observed.

*Spur*.—Length: Approximately 1.8 cm. Diameter at proximal end: Approximately 3.0 mm. Diameter at distal end: Approximately 1.0 mm. Texture: Sparsely pubescent. Color: Closest to 161C with overlays of 48C and 144D.

*Pedicels*.—Strength: Strong. Aspect: Acute angle to stem. Length: Approximately 2.7 cm. Diameter: Approximately 2.0 mm. Texture: Densely pubescent. Color: 146A occasionally with an overlay of 187A.

*Reproductive organs*.—Androecium: Stamen quantity: 19 per flower. Stamen length: Approximately 9.0 mm, twisted. Anther shape: Oblong. Anther length: Approximately 1.0 mm. Anther color: 7B. Filament color: NN155D with a faint tint of 52B nearest anther. Pollen amount: Sparse. Pollen color: NN155D. Gynoecium: Pistil quantity: 4 to 6 per flower. Pistil length: Approximately 1.4 cm in mature flower. Stigma shape: Bifid. Stigma color: NN155D transitioning to N186C in mature flower. Style length: Approximately 3.0 mm in mature flower. Style color: NN155D with an overlay of 55B, transitioning to N186C in mature flower. Ovary length: Approximately 1.1 cm in mature flower.

Ovary texture: Moderately pubescent. Ovary color: 161C with streaks of 55B, transitioning to 144A in mature flower.

Seed and fruit production: Neither seed nor fruit production has been observed.

Disease and pest resistance: Resistance to pathogens and pests common to *Delphinium* has not been observed.

What is claimed is:

1. A new and distinct cultivar of *Delphinium* plant named 'Red Lark', substantially as herein illustrated and described.

* * * * *